United States Patent [19]
Charles

[11] Patent Number: 5,689,849
[45] Date of Patent: Nov. 25, 1997

[54] BIO MECHANICAL CORRECTIVE DEVICES

[76] Inventor: Robert Charles, 49a Stephens Terrace, St. Peters, South Australia, Australia, 5069

[21] Appl. No.: 605,039
[22] PCT Filed: Jan. 6, 1995
[86] PCT No.: PCT/AU95/00004
  § 371 Date: Mar. 7, 1996
  § 102(e) Date: Mar. 7, 1996
[87] PCT Pub. No.: WO95/31161
  PCT Pub. Date: Nov. 23, 1995

[30] Foreign Application Priority Data

May 12, 1994 [AU] Australia .................... 651550

[51] Int. Cl.⁶ .................................................. A43D 7/14
[52] U.S. Cl. ........................ 12/146 M; 12/142 N; 36/88
[58] Field of Search ................... 36/88, 93, 140; 12/142 N, 146 M

[56] References Cited

U.S. PATENT DOCUMENTS

| | | | |
|---|---|---|---|
| 2,120,987 | 6/1938 | Murray | 12/142 N |
| 2,177,304 | 10/1939 | Murray | 12/142 N |
| 2,688,760 | 9/1954 | Forte. | |
| 2,786,282 | 3/1957 | Falk. | |
| 2,973,529 | 6/1961 | Silverman | 12/142 N |
| 3,262,142 | 7/1966 | Keder | 12/142 N |
| 4,567,617 | 2/1986 | Limbach | 36/93 |
| 4,669,142 | 6/1987 | Meyer | 12/146 M |
| 4,747,410 | 5/1988 | Cohen. | |
| 4,868,945 | 9/1989 | DeBettignies. | |
| 5,036,851 | 8/1991 | Cohen. | |
| 5,069,212 | 12/1991 | Cohen. | |
| 5,164,878 | 11/1992 | Hauser. | |

FOREIGN PATENT DOCUMENTS

| | | |
|---|---|---|
| GB2067199A | 7/1981 | United Kingdom. |
| PCT/AU90/00543 | 5/1991 | WIPO. |
| PCT/US92/00292 | 7/1992 | WIPO. |

Primary Examiner—M. D. Patterson
Attorney, Agent, or Firm—Marshall & Melhorn

[57] ABSTRACT

The present invention relates to bio mechanical corrective devices, commonly known as orthotics, which are used to support the foot and to correct musculo-skeletal misalignments. A method of manufacture of an improved orthotic and an orthotic made by the method are disclosed.

6 Claims, 6 Drawing Sheets

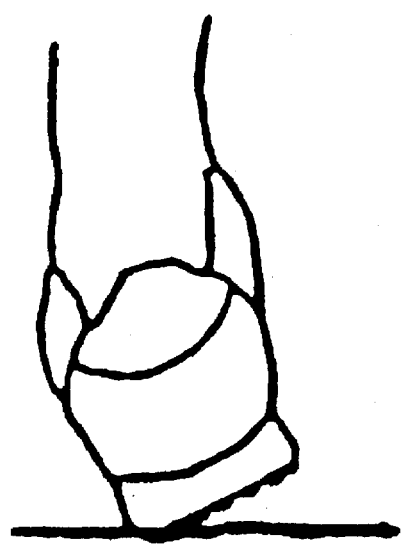
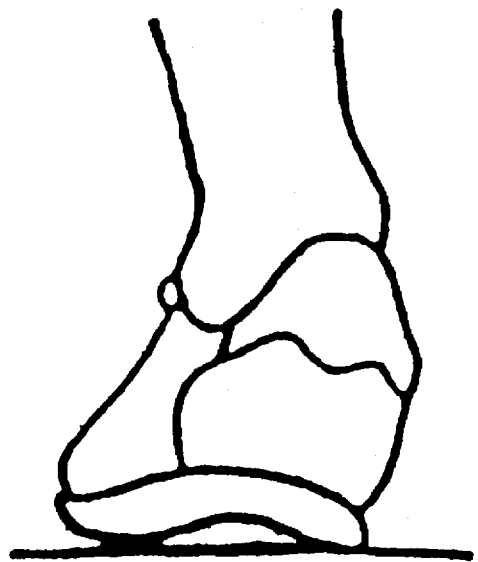
FIG 2A  FIG 2B
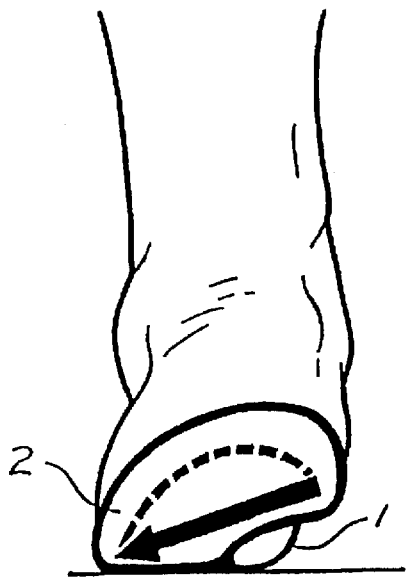
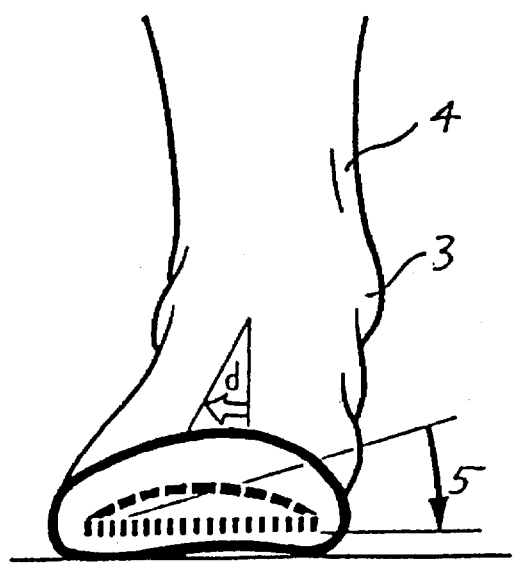
FIG 3A  FIG 3B

BIO MECHANICAL CORRECTIVE DEVICES

BACKGROUND ART

Orthotic shoe inserts are known as a means of providing support to the foot to assist in correcting bio mechanical stresses in the lower skeleton. Known orthotics take many forms but fall into two main categories:

1. Rigid arch supports which primarily support the heel and arch but provide little or no support to the forefoot; and
2. Soft, flexible full foot supports which primarily provide shock protection while providing some arch support.

In recent years people have become aware that skeletal misalignment can lead to hip, leg, knee, ankle and foot injuries. A number of text books have been written which describe the bio mechanics of human movement and one such text which is incorporated herein by reference is 'Bio mechanics—A qualitative approach for studying human movement' by E. Kreighbaum and K. M. Barthels.

The inventor has realised that a primary cause of injury or discomfort in the lower skeleton and associated muscles is due to misaligned foot contact with the ground. Two primary forms of misalignment occur: eversion—misalignment of the heel leading to a rolling in of the ankle; pronation—misalignment of the forefoot leading to a rolling of the foot.

Prior art orthotics have not addressed the need for precise correction of the misalignment of the foot. When the rolling has been identified the prior art devices have attempted to correct the roll by placing an angle under the heel or by exaggerating the arch support. Neither of these approaches provide the necessary precision to alleviate the musculo-skeletal stresses. In fact, incorrectly or inaccurately placed corrections can result in extra musculo-skeletal stresses such as: heel roll-out on contact with the ground due to excessive angle under the heel; leg rotation due to excessive arch support; increased forefoot roll from either or both of the above.

Prior art orthotics such as those produced by the method of Wynd (Australian patent Application Number 46469/89) seek to correct the rolling by producing an orthotic from a cast taken of the foot when the sub-talor joint is in neutral position with the forefoot fully pronated about both the mid tarsal joint longitudinal and oblique axes. The Wynd method does not result in a correctly shaped orthotic because the cast is made when the foot is in the wrong position. Having the forefoot fully pronated changes the shape of the arch compared to the shape of the arch when the leg is in the erect weight bearing position. The orthotic formed does not restore the arch to its correct structure in terms of both the longitudinal and transverse arch shape.

In other prior art approaches a cast is taken of the foot with the foot plantar flexed or pointed. The cast is then modified to suit the concept of the short orthotic. Typically this involves modification of the cast by removal of some material and build up in other areas. An orthotic is made to conform to the resultant cast. While the modifications of the cast may lead to a convenient foot shape it does not take into account the full musculo-skeletal system of the lower body. It has also become clear to the inventor that restoring the arch is only part of the requirement. Correction of the contact angles of the foot with the ground can affect the entire lower body musculo-skeletal system.

Posture and therefore the planes of motion of joints is determined by bone structure not muscles. The skeletal alignment sets the line of muscular action therefore imperfections in the skeletal structure leads to muscular injury.

Most people have some degree of skeletal misalignment which will lead to joint, muscle and tendon injury during intensive activity. To eliminate joint, muscle and tendon injuries the skeletal alignment must be altered so as to correct the mechanical function and eliminate injury causing movements.

Correcting the mechanical function of the musculo-skeletal system of the body achieves movement without excessive wear and gives correct balance, shock absorption and weight distribution. This improvement in the mechanics of movement lessens the need for muscles to stabilise therefore improving efficiency of exercise and minimising physiological effort. The capacity of the driving muscles to work is increased by retaining mechanical alignment through their working range of movement thus giving better performance and greater training effect.

When walking the correct sequence of events is that the foot lifts from the ground and the leg swings forward at the hip with the knee bent. As the leg reaches the extent of its forward motion the knee straightens and the heel strikes the ground. Weight is transferred from the heel to the forefoot and the cycle continues. The sequence of actions in running is similar.

It is clear that the foot forms a platform for the motion of other parts of the skeleton. If the foot does not form a stable and well positioned platform a range of problems can be caused. It will be appreciated that if the heel does not strike the ground squarely the foot will roll thereby placing stress on the lower leg and knee. Misalignment between the ground and heel or ground and forefoot causes a loss of leg alignment during gait which results in injury to working joints, muscles and tendons. The forceful rolling in of the foot due to the foot striking the ground on an outer edge is known as over pronation and is a primary manifestation of skeletal misalignment.

Healthy movement depends on correct skeletal alignment which dictates posture and body movement. A misaligned skeleton results in excessive wear/injury which often builds up over time resulting in recurring injuries. Various forms of manipulation and medication can temporarily alleviate the symptoms of skeletal misalignment but cannot correct the inherent faults.

Other postural faults which can lead to stress injuries include:

Abducted feet—This problem occurs at the ankle and is often associated with internally rotated legs. It results from a foot which is misaligned on its contact with the ground such that the foot strikes on an outer edge and rolls in causing the foot to hinge at the ankle and angle outward away from the centre line of the body. This leads to instability and excessive pronation.

Ankle Collapse—This problem occurs when the foot strikes the ground at an angle more commonly on an outer edge thereby rolling inward and causing the ankle to collapse medially (or fall inward). This leads to stresses in the skeleton above the ankle as realignments occur.

Hyper extended or lock back knees—This problem results from internally rotated knees which lock back causing a change in hip alignment and the centre of gravity of the body. As a result the pelvis rotates forward and causes excessive lordosis (curvature) in the lower spine. The curvature places strain on the vertebra which can cause back pain and nerve damage.

OBJECT OF THE INVENTION

The inventor has found that in order to accurately correct misalignments in the lower skeleton and to relieve musculoskeletal stresses it is necessary to form an orthotic from a cast taken of the foot with the lower limbs in a position which replicates a normal weight bearing position during dynamic movement of the body.

One intended object of the present invention is to provide a method of producing an orthotic which provides a stable platform to correct angles of contact for the foot when contacting the ground during motion.

A further object of the invention is to provide an orthotic which promotes correct mechanical function and substantially eliminates rolling most commonly (pronation/eversion) of the foot thereby providing relief from musculoskeletal stresses including abducted feet, pronation, ankle collapse, back ache, heel spur, runners knee, shin splints, sprains and strains.

DISCLOSURE OF THE INVENTION

In one form of the invention there is provided a method of manufacture of an orthotic comprising the steps of:

taking an imprint of the foot with the foot in a position which replicates a normal weight bearing position;

making a positive cast of the foot from the imprint;

measuring the angles of the cast to determine the degree of forefoot roll and heel roll;

forming the orthotic by moulding material to the cast;

shaping the underside of the orthotic by angling the heel and forefoot regions to correct heel roll and forefoot roll of the foot; and detaching the orthotic from the cast.

In preference the step of forming the orthotic further comprises the steps of forming a first layer of the orthotic by moulding a thin section of material to the cast;

forming a second layer of the orthotic by moulding and affixing a thick section of said material to the first layer;

In a further form of the invention there is proposed an orthotic formed from high density closed cell synthetic rubber, said orthotic having a shape on an upper side adapted to match the underside of a foot and having angles on an underside adapted to provide a stable platform for the foot when the foot contacts the ground.

BRIEF DESCRIPTION OF THE DRAWINGS

To further assist in understanding the invention reference will be made to the following drawings in which:

FIGS. 2A and 2B Schematically shows skeletal stress due to foot roll;

FIGS. 3A and 3B Schematically shows skeletal stress due to forefoot roll;

FIG. 8 Shows in detail the correct position for taking the foot imprint of FIG 7a.

DETAILED DESCRIPTION OF THE DRAWINGS

Figure 1A:
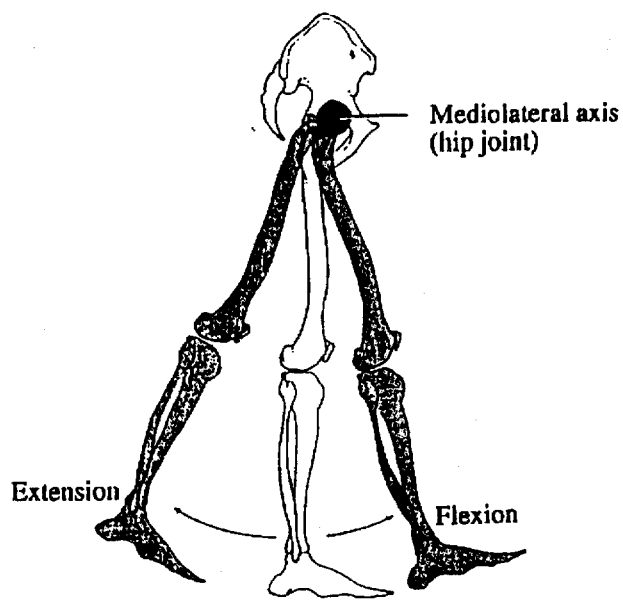
FIGS. 1A, 1B, 1C, and 1D Shows examples of the skeletal system of the lower extremities.
Figure 1B:
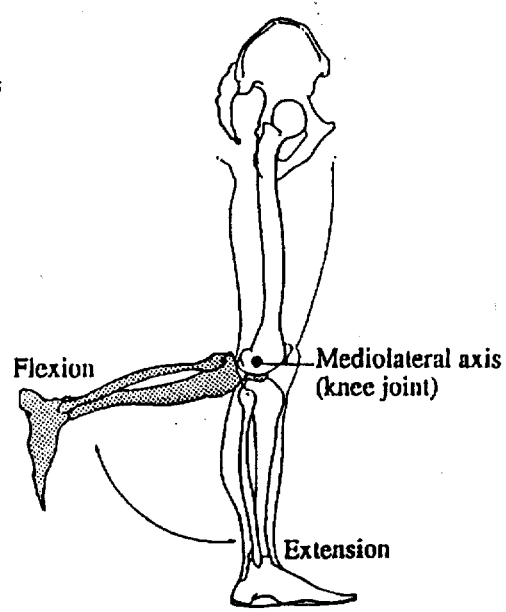
Figure 1C:
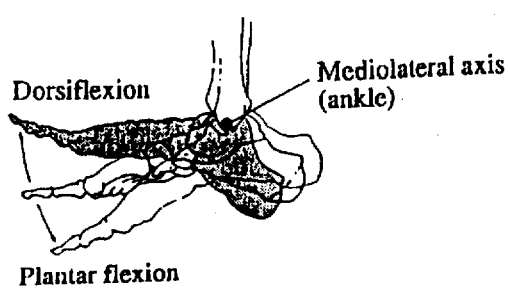
Figure 1D:
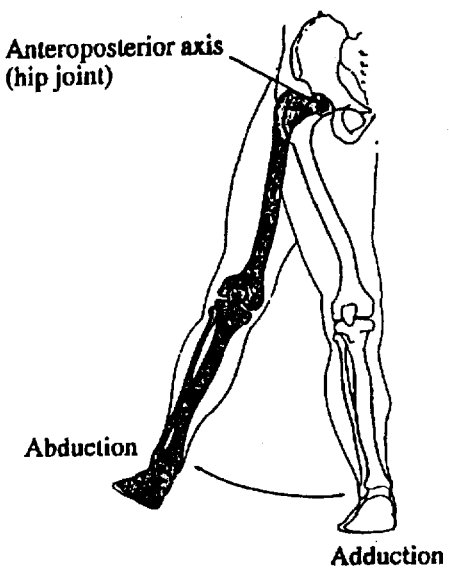

Referring now to the drawings in detail there is shown in FIG. 1 the interaction of various parts of the lower skeleton. The most basic law of biomechanics is that each joint in the body has a line of movement known in biomechanics as a 'plane of motion'. The hip joint has a principal plane of motion as shown in FIG. 1a and a secondary plane shown in FIG. 1d. The knee is essentially a straight hinge having a single line of motion as shown in FIG. 1b. The ankle has a plane of motion as shown in FIG. 1c as well as the ability to rotate.

FIG. 2 shows the skeletal stresses associated with the heel rolling after the foot strikes the ground. In FIG. 2a the heel and forefoot are shown as striking the ground on one side with the other side slightly raised. As shown in FIG. 2b this must lead to the heel rolling to the right to complete contact with the ground. The rolling of the heel pulls the ankle inwards and downwards forcing realignment of the leg, knee and hip joints. The realignments require movements not strictly within the planes of motion depicted in FIG. 1 and therefore lead to stress and strain on muscles, tendons and bones. Heel roll-in can lead to osteo-arthritis in the hip as well as hamstring and achilles tendon injuries.

FIG. 3 shows the skeletal stresses associated with the forefoot rolling. In FIG 3.a the heel 1 has struck the ground squarely but as weight is transferred to the forefoot 2 (shown cut away) one side contacts the ground before the other side. The forefoot 2 will roll pulling the ankle 3 and leg 4 out of alignment, as shown in FIG. 3.b, which leads to stress and strain as in the situation depicted in FIG. 2. The amount of forefoot roll is measured by the angle shown by arrow 5.

Figure 4:
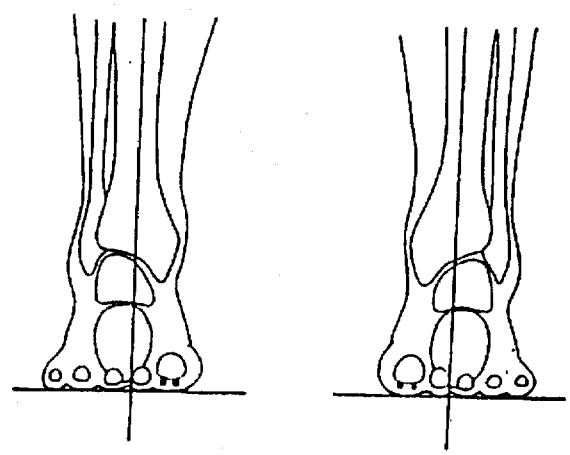
FIG. 4 Shows the theoretical ideal alignment of the feet.
Figure 5:
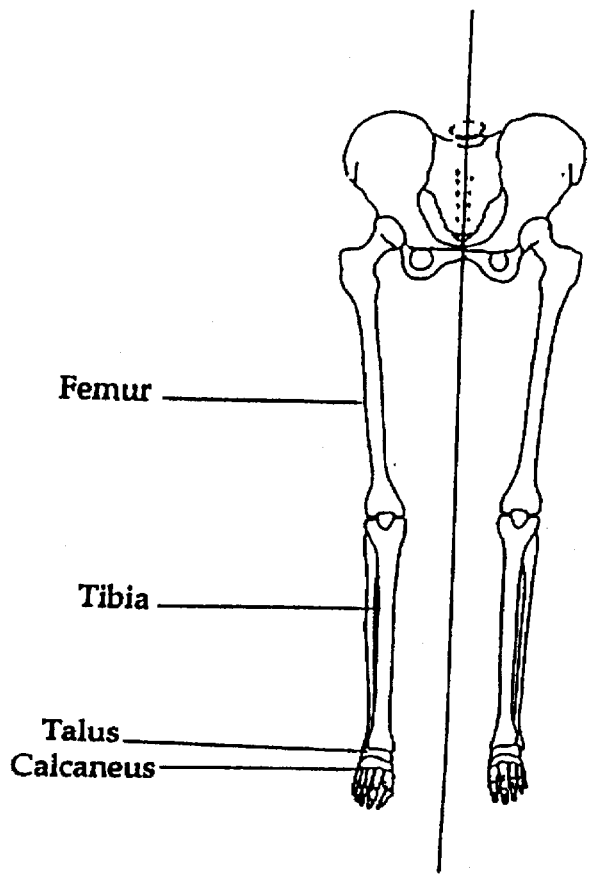
FIG. 5 Shows the theoretical ideal alignment of the lower skeleton.

FIG. 4 shows the ideal alignment of the feet. The heel and forefoot are flat on the ground. The ankle is level and the longitudinal axis of the foot is parallel with the mid-sagittal axis of the body plane. FIG. 5 shows the ideal alignment of the lower skeleton, the tibia is vertical and the femur is slightly inclined to allow for the width of the pelvis.

Figure 6:
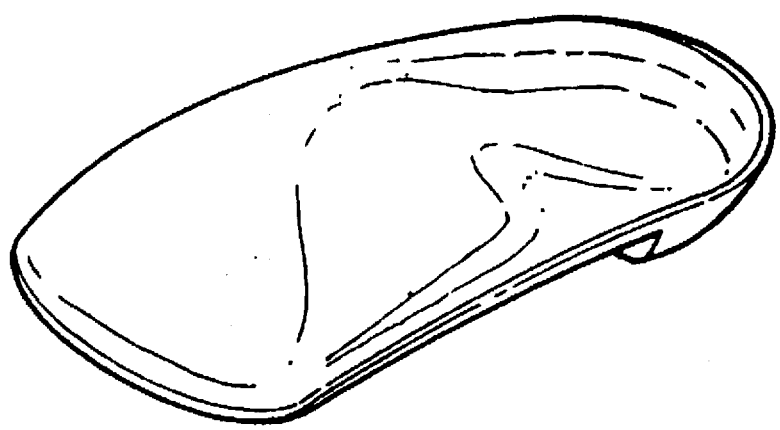
FIG. 6 Shows an orthotic formed in accordance with a prior art method.

Unfortunately, commonly occurring skeletal variations (e.g. bowed legs) cause excessive angles of contact. Prior art orthotics, such as that depicted in FIG. 6, have attempted to provide correction to the foot to achieve this ideal alignment. In so doing these orthotics create stress and strain by forcing the lower skeleton to assume an unnatural position. The present invention aims to form a stable platform for the foot without introducing additional stresses by theoretical correction of the foot position.

FIG. 7 shows the steps associated with the method of the present invention.

Figure 7A:
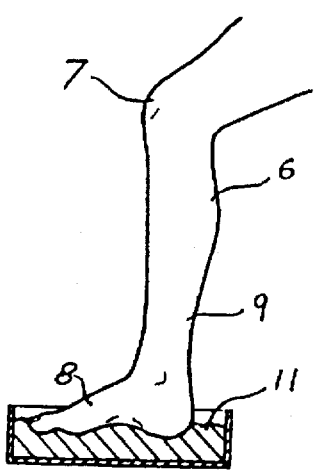
FIGS. 7A, 7B, 7C, 7D, and 7E Shows the steps involved in producing the orthotic of the present invention.
Figure 7B:
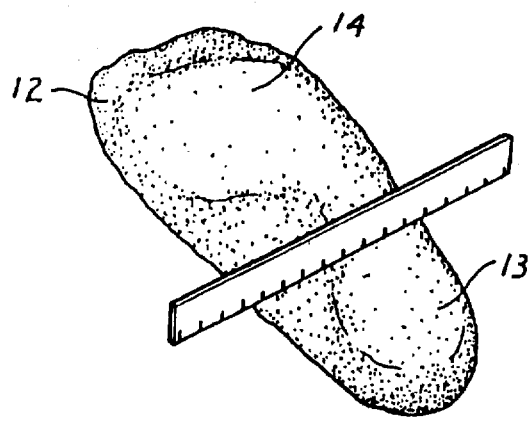
Figure 7C:
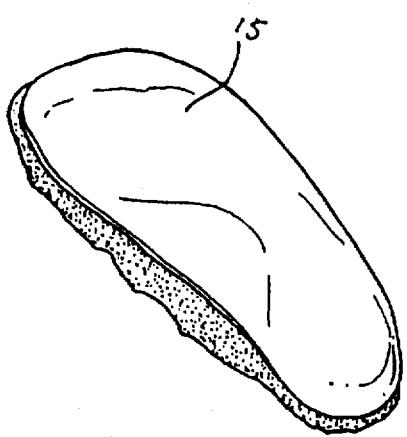
Figure 8B:
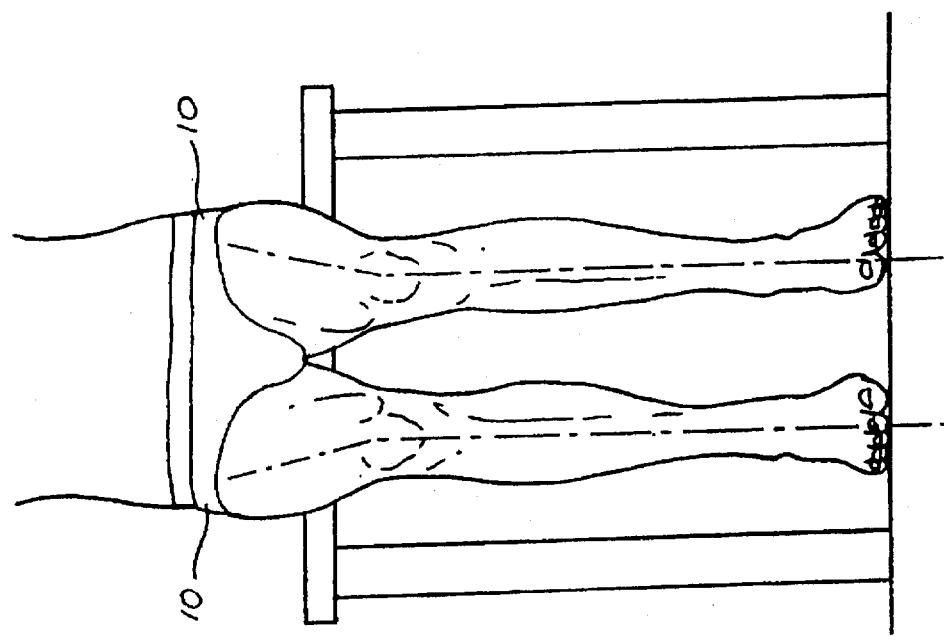
Figure 8A:
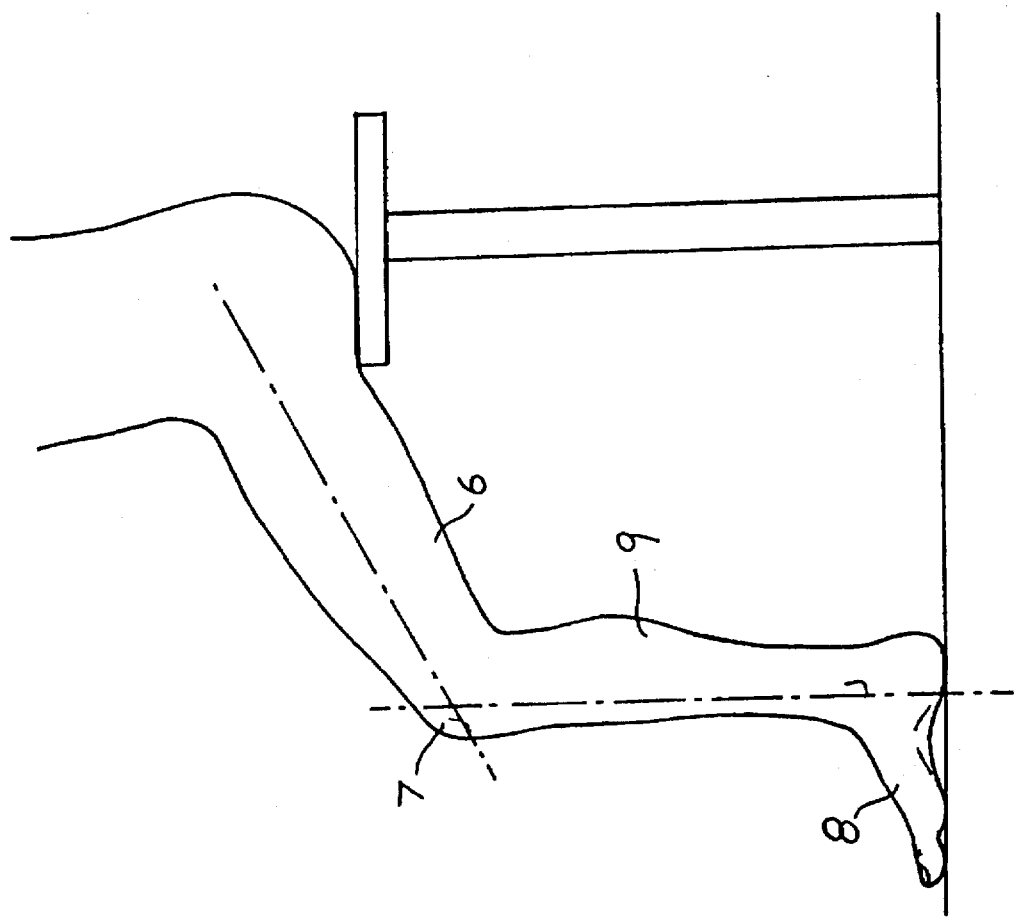

FIG. 7a and FIG. 8 show the correct position of the leg for taking a cast of the foot. The leg 6 is bent at the knee 7 at an angle of knee flexion greater than 90 degrees (approximately 135 degrees in the example), and the lower leg 9 is vertical with the foot 8 directly below the knee 7. The knee 7 is inside the width of the hips 10 and facing forward in the sagittal plane as determined in individuals by moving the knee through its range of movement as shown in FIG. 8b with the feet straight ahead and parallel. The feet will be slightly rolled as shown in FIG. 8.b. The angle of the roll will vary as the position of the legs is changed, thus it is important to correctly align the legs for accurate casting of the foot.

An imprint 11 of the foot 8 is taken in this position. A positive cast 12 is made from the imprint and the cast is examined to determine the angles of contact of the heel 13 and forefoot 14.

A thin layer 15 of a high density, closed cell synthetic rubber material is heated and moulded to the cast 12 to form the first layer of the orthotic. A commercially available material known as EVA is chosen for its thermoplastic properties. EVA is a high density, closed cell synthetic rubber compound which does not squash but is flexible. When heated to temperatures of approximately 50 degrees Celsius it becomes mouldable. Upon cooling it retains the moulded shape. Other materials having similar properties would also be appropriate for forming the orthotic.

Figure 7D:
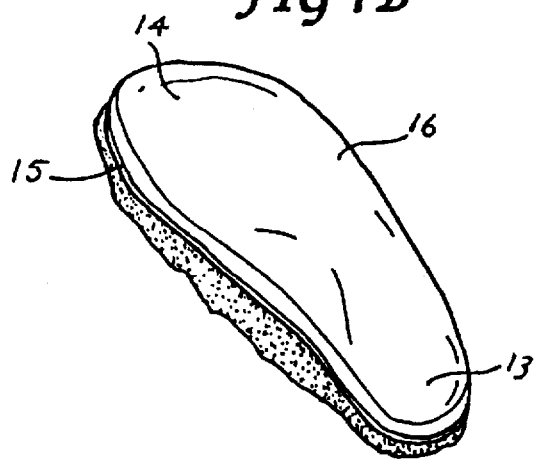
Figure 7E:
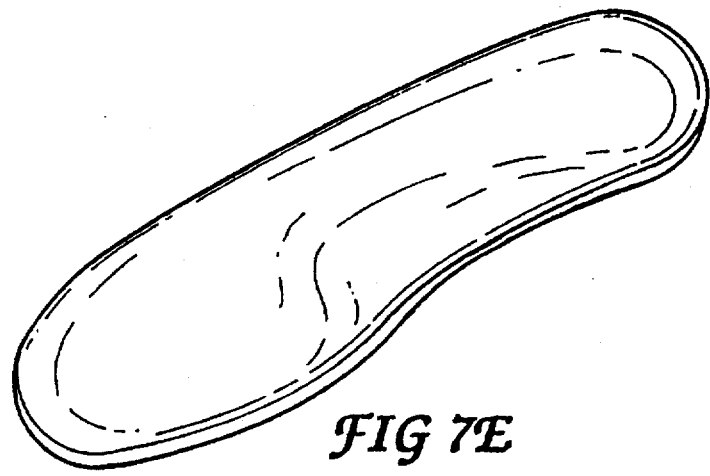

As depicted in FIG. 7d a thick layer 16 of the same material is heated and glued to the thin layer. The two layers together form the final orthotic. A two step approach is used to ensure that the final orthotic complies to the shape of the cast 12.

Angular corrections to the underside of the orthotic in the heel 13 and forefoot 14 regions are made to produce the finished orthotic shown in FIG. 6e. The corrections are made by grinding the underside of the orthotic to correct the angles measured in the step shown in FIG. 7b.

The orthotic herein disclosed realigns the bones and joints into their correct plane of motion thereby alleviating many running and walking injuries. The orthotic can correct the following commonly occurring running and walking injuries:

Plantar Faciitis (heel spur)—Pain to the heel caused by overstressing and tearing of the attachment at the heel of the long ligament which crosses the arch. This condition is caused by the excessive force when over pronation transfers excessive weight onto the arch.

Chondromalacia patella (runners knee)—Damage to the smooth surfaces inside the knee joint caused by the kneecap being pulled sideways when the knee collapses and/or internally rotates as a result of over-pronation.

Illiotibial Band Syndrome—Damage to the band of tendon attaching the muscles of the outside of the thigh to the side of the knee joint due to sudden forceful internal rotation of the leg which occurs during over pronation.

Shin splints—Aching in the shin bone area due to the torsional or twisting forces which result from over pronation.

The postural alignment orthotics herein described are individually prescribed, full length, flexible, semi-rigid, light weight appliances worn in shoes and used in weight bearing activity. They move with the foot but maintain structural support to adjust foot contact with the ground thereby aligning and stabilising the lower musculo-skeletal system into correct line of movement. Variations on the method of production of the orthotic of this invention will be evident to those skilled in the art and can be made without departing from the scope of the invention.

I claim:

1. A method of manufacture of an orthotic comprising the steps of:

taking an imprint of the foot;

making a positive cast of the foot from the imprint;

measuring angles of contact of the cast to determine the degree of forefoot roll and heel roll;

forming the orthotic by moulding material to the cast;

shaping the underside of the orthotic by angling the heel and forefoot regions to correct heel roll and forefoot roll of the foot; and detaching the orthotic from the cast, wherein the step of taking the imprint of the foot includes having a subject seated at a height such that the leg is bent at the knee at an angle of knee flexion of greater than 90 degrees with the foot contacting the ground, positioning the knee whereby the knee is facing forward in the sagittal plane, as determined by moving the knee through its normal range of movement, which will position the upper leg in correct alignment with respect to the hip and torso, positioning the lower leg vertically, the heel directly below the knee from a side on view, with both feet straight ahead and parallel with respect to one another, and positioning the ankle join in correct alignment as determined visually.

2. The method of claim 1 wherein the step of forming the orthotic further comprises the steps: forming a first layer of the orthotic by moulding a thin section of material to the cast; forming a second layer of the orthotic by moulding and affixing a thick section of said material to the first layer.

3. The method of claim 1 wherein the leg is bent at an angle in the range of 120 degrees to 150 degrees.

4. The method of claim 1 wherein the material is substantially incompressible but flexible at normal temperatures and mouldable at elevated temperatures.

5. The method of claim 4 wherein the material is a high density, closed cell synthetic rubber material.

6. The method of claim 2 wherein the second layer is affixed to the first layer by gluing.

* * * * *